United States Patent [19]

Hobbs

[11] 3,956,386

[45] May 11, 1976

[54] CIS-N,N,N',N'-TETRAMETHYLCYCLOPROPANE-1,2-DICARBOXAMIDE AND USE THEREOF

[75] Inventor: Charles F. Hobbs, Des Peres, Mo.

[73] Assignee: Monsanto Company, St. Louis, Mo.

[22] Filed: May 26, 1971

[21] Appl. No.: 147,242

[52] U.S. Cl............................ 260/557 R; 71/118
[51] Int. Cl.²................................. C07D 103/737
[58] Field of Search............................ 260/557

[56] References Cited
UNITED STATES PATENTS 3,352,910  11/1967  Smith et al........................ 260/557
3,360,432  12/1967  Newallis et al. .................. 260/557
3,484,485  12/1969  Schwartz........................... 260/557

OTHER PUBLICATIONS

Shono et al., Chem. Abstracts, Vol. 65, item 3051d-h and 3052a-b, (1965).
Blomquist et al., J. Am. Chem. Soc., Vol. 81, p. 2012–2017, (1959).

*Primary Examiner*—Harry I. Moatz
*Attorney, Agent, or Firm*—Arnold H. Cole

[57] ABSTRACT cis-N,N,N',N'-Tetramethylcyclopropane-1,2-dicarboxamide as a new chemical compound, and the use thereof in the regulation of plant growth.

1 Claim, No Drawings

CIS-N,N',N'-TETRAMETHYLCYCLOPROPANE-1,2-DICARBOXAMIDE AND USE THEREOF

This invention relates to a novel composition of matter which is a derivative of cyclopropanedicarboxamide and to the use of said derivative as a plant growth regulator. More particularly, this invention is concerned with cis-N,N,N',N'-tetramethylcyclopropane-1,2-dicarboxamide. This compound has been found to display useful and unexpected properties in regulating certain plant growth.

The novel compound of this invention can be prepared by reacting dimethyl cis-1,2-cyclopropanedicarboxylate with dimethylamine. The starting material for such a reaction is obtained in the following manner.

A suitable reaction vessel equipped with a stirrer and a condenser is charged with 39.2 grams (0.35 mole) of cis-cyclopropane-1,2-dicarboxylic anhydride and 100 ml. of anhydrous methanol. It is heated at reflux temperature for about 3 hours and allowed to cool. The methanol is removed by stripping, and 80 grams (0.38 mole) of phosphorus pentachloride is added slowly with cooling. There is also added 40 ml. of toluene, after which the mixture is heated to 110°C. and then allowed to cool. Toluene and hydrogen chloride are removed by stripping. The acid chloride product is treated with 100 ml. of methanol with cooling, and the mixture is thereafter heated at reflux temperature for 2 hours, cooled and stripped of excess methanol. Ether is then added, and the mixture is washed, dried, filtered and stripped of ether. A red-orange residual oil is distilled, and a product is collected at b.p. 60°–65°C. (0.20 mm). On redistillation, the cut at b.p. 45°–51°C. (0.07 mm) is dimethyl cis-1,2-cyclopropanedicarboxylate in a yield of 39.2 grams.

A pressure bottle is charged with 10.0 grams (0.063 mole) of the dicarboxylate so obtained, and 85 ml. of pre-cooled anhydrous dimethylamine is added thereto. The mixture is heated in an oil bath at 80°C., after which it is permitted to stand while dimethylamine evaporates. The residual semi-solid mass is then filtered and recrystallized from tetrahydrofuran to yield 2.7 grams of cis-N,N,N',N'-tetramethylcyclopropane-1,2-dicarboxamide, m.p. 103°–104°C.

An alternative procedure for preparing the compound of this invention involves the treatment of a mixture of cis and trans-dimethyl cyclopropane-1,2-dicarboxylate with excess dimethylamine. A pressure bottle is charged with 25.3 grams (0.16 mole) of the mixed dicarboxylate and cooled. There is added 90 grams (2.0 moles) of pre-cooled anhydrous dimethylamine, and the mixture is allowed to warm slowly to room temperature. It is thereafter heated in an oil bath at about 50°–60°C. for about 9 days. Dimethylamine is then allowed to boil off, after which further dimethylamine and methanol are removed on an aspirator. The semi-solid residue is distilled, and the fraction obtained at 115°–145°C. (0.25 mm) is recrystallized twice from tetrahydrofuran. The product is obtained as white plates, m.p. 103°–104.5°C., and it is identified as cis-N,N,N',N'-tetramethylcyclopropane-1,2-dicarboxamide by nuclear magnetic resonance.

Elemental analysis found 58.41% carbon, 8.63% hydrogen and 14.77% nitrogen as against calculated values of 58.67%, 8.75% and 15.21% respectively for $C_9H_{16}N_2O_2$.

The chemical of the present invention may be applied to plants, which term includes various plant parts such as seeds, flowers, fruits, vegetables, roots and foilage in various manners. Seeds may be treated directly with the chemical before planting, or seeds may be treated with the chemical by incorporating the chemical in the soil before or after planting the seeds. The chemical may be applied to plants in an inert medium as a dust in admixture with a powdered solid carrier, such as the various mineral silicates, e.g., mica, talc, pyrophllite and clays or as an aqueous composition. The chemical may be applied in admixture with small amounts of surface-active wetting agents, which may be anionic, non-ionic, or cationic surface-active agents, generally as aqueous compositions. The chemical may be dissolved in organic solvents such as acetone, benzene, or kerosene, and the solutions of the chemical emulsified in water with the air of surface-active agents. Such surface-active agents are well known and reference is made to U.S. Pat. No. 2,547,724, columns 3 and 4, for detailed examples of the same. The chemical of the invention may be admixed with powdered solid carriers, such as mineral silicates, together with a surface-active agent so that a wettable powder may be obtained which may be applied directly to plants, or which may be shaken up with water for application to the plants in that form.

The useful and unexpected properties of the chemical of this invention are illustrated in the following exemplary tests.

EXAMPLE A

A number of corn plants of the Pioneer 3567 variety are grown from seeds in an aluminum pan for a period of one week. The height of each corn plant is then measured to the top of the whorl. A 1% solution of the chemical of this invention in acetone is prepared, and a 2.0 ml. portion of said solution is mixed with 0.8 ml. of acetone and 2.8 ml. of a water mixture with 0.05% of Aerosol OT. The resultant solution is then sprayed over the plants in the pan at an application rate equivalent to 6.0 lbs./acre. A control pan, planted at the same time as the test pan, also has its plants measured, but receives no chemical application. The pans are transferred to a greenhouse and watered from below in a sand bench. Each pan is fertilized with 40 ml. of a 1.5% solution of Rapid-Gro about 2 days after treatment.

Two weeks after treatment the height of each plant in the pans is again measured to the top of the whorl. After determining the average height increase of the plants in the untreated control pan, it is found that at least two-thirds of the corn plants treated with the compound of this invention show 26% or more stature reduction by direct comparison.

EXAMPLE B

In this test corn plants of the XL-45 variety are grown from seeds in individual plastic pots. After four weeks of growth, the height of each plant is measured to the base of the flag leaf. The plants are then sprayed with a solution of the chemical of this invention at an application rate equivalent to 8.33 lbs./acre, transferred to a greenhouse, and watered and fertilized as set forth above.

Three weeks after treatment the height of the plant in each pot is again measured to the base of the flag leaf, and an average height is calculated for the untreated control plants. It is found that all of the corn plants treated with the chemical of this invention were of a total height at least 15% less than the average of the plants in the control.

In selecting appropriate rates of application for use of the compound of this invention, it will be recognized that precise dosages will be dependent upon the plant species being treated, the particular plant part or habitat to which application is made, the age or development stage of the plant, and various other factors well known to those skilled in the art. In connection with the specific application rates recited in Examples A and B in terms of lbs./acre, it should further be recognized that the former involves a relatively few plants in a 52 in.$^2$ pan, and the latter involves a single plant in an 8 in. diameter pot. Thus, the application of the chemical to the plants themselves is generally at a rate somewhat less than the stated lbs./acre.

The compound of this invention can be employed at rates of from about 0.05 to about 10.0 lbs./acre, and it is preferred to use an application rate of at least about 0.1 lbs./acre.

The growth inhibition or stature reduction demonstrated herein by the compound of this invention is a valuable feature in plant growth regulation. Reducing the stature of crop plants permits an increase in the plant population in a given growing area and will often result in significant increase in yield. In addition, such reduction of stature increases accessibility to the field for other treatments, cultivation and ultimate harvesting. It has been found that reduced stature of certain plants also decreases the incidence of pest infestation. At the same time, such plants may demonstrate increased resistance to drought and/or increased cold hardiness.

The desirable plant growth regulating properties of cis-N,N,N',N'-tetramethylcyclopropane-1,2-dicarboxamide are particularly unexpected since very closely related compounds do not perform in the same manner. The geometric trans isomer, reported in J.A.C.S., V. 81, pg. 2016 (1959) and J.A.C.S., V. 91, pg. 780 (1969), was tested in the manner described in Example A, as was the cis-tetraethyl homolog of the compound of this invention. Neither of these compounds demonstrated any significant stature reduction in the corn plants, and both were categorized as inactive.

While the invention has been described herein with regard to certain specific embodiments, it is not so limited. It is to be understood that variations and modifications thereof may be made by those skilled in the art without departing from the spirit and scope of the invention.

What is claimed is:
1. cis-N,N,N',N'-Tetramethylcyclopropane-1,2-dicarboxamide.

* * * * *